Figure 1:
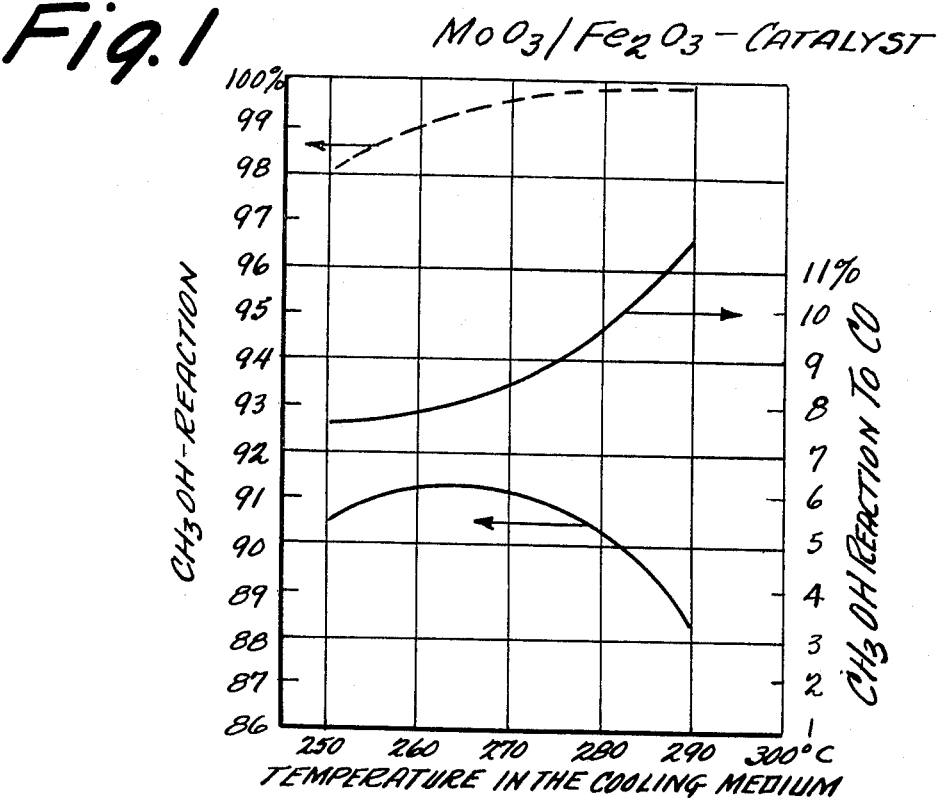

United States Patent [19]

Friedrich et al.

[11] 3,978,136

[45] Aug. 31, 1976

[54] PROCESS FOR THE PRODUCTION OF A CATALYST SUITABLE FOR THE OXIDATION OF METHANOL TO FORMALDEHYDE

[75] Inventors: Heinz Friedrich; Walter Neugebauer, both of Constance, Germany

[73] Assignee: Deutsche Gold- und Silber-Scheideanstalt vormals Roessler, Germany

[22] Filed: Mar. 14, 1974

[21] Appl. No.: 451,291

Related U.S. Application Data

[62] Division of Ser. No. 285,540, Aug. 31, 1972, Pat. No. 3,843,562.

[30] Foreign Application Priority Data

Sept. 14, 1971 Germany............................ 2145851

[52] U.S. Cl............................................. 260/603 R
[51] Int. Cl.².......................................... C07C 45/16
[58] Field of Search.................... 260/603 HF, 603 R

[56] References Cited

UNITED STATES PATENTS

| | | | |
|---|---|---|---|
| 1,735,763 | 11/1929 | Jaeger................................. | 260/603 |
| 2,812,309 | 11/1957 | Allyn et al. ......................... | 260/603 |
| 3,459,807 | 8/1969 | Aglietti et al. ...................... | 260/603 |
| 3,640,900 | 2/1972 | McClellan et al. ................. | 260/603 |
| 3,843,562 | 10/1974 | Friedrich et al. ............... | 260/603 R |

OTHER PUBLICATIONS

Klisurski, C. Abst., vol. 66, 108707n (1967).
Tsutomu et al., Chem. Abst., vol. 69, 61851z (1968).

*Primary Examiner*—James O. Thomas, Jr.
*Assistant Examiner*—James H. Reamer
*Attorney, Agent, or Firm*—Cushman, Darby & Cushman

[57] ABSTRACT

Catalysts for the oxidation of methanol to formaldehyde are prepared having an $MoO_3:Fe_2O_3$ weight ratio below 10:1 by coprecipitating dissolved molybdenum and iron compound, mixing up to 90% of titanium dioxide with the coprecipitate, molding the mixture and finally calcining at elevated temperature.

10 Claims, 2 Drawing Figures

PROCESS FOR THE PRODUCTION OF A CATALYST SUITABLE FOR THE OXIDATION OF METHANOL TO FORMALDEHYDE

This is a division of application Ser. No. 285,540, filed Aug. 31, 1972, now U.S. Pat. No. 3,843,562.

The present invention is directed to a process for the production of a catalyst for the oxidation of methanol with oxygen containing gases, e.g., air or oxygen, to formaldehyde in which there are used oxide compounds of molybdenum and iron having a weight ratio of $MoO_3:Fe_2O_3$ below 10:1. The invention also concerns the use of the catalyst to make formaldehyde from methanol.

Formaldehyde can be produced by the oxidation of methanol with air or oxygen in the presence of oxidic catalysts, especially those that contain molybdenum and iron oxides. Since the reaction is strongly exothermic in the industrial carrying out of the methanol oxidation there are used tube bundle reactors from which the heat of reaction can be removed by a cooling medium. The catalysts are most commonly filled into the reaction tubes in the form of extrusions or tablets measuring between 2 and 4 mm.

Because of a continual improvement in the catalyst the yields in this process are high, they are stated to be 90 to 94%. Besides the production of high yields there are further requirements on the catalysts in order that the process can be carried out in an industrially and economically satisfactory manner. Among these further requirements it is especially important that the shaped catalyst bodies have high mechanical strength; high space-time-yield and low cost of the production.

The present invention is based on the problem of developing a process for the production of a catalyst for the oxidation of methanol with an oxygen-containing gas, preferably air, with a content of an oxidic combination of molybdenum and iron with an $MoO_3:Fe_2O_3$ weight ratio below 10:1 and which can be much lower, e.g., 3.9:1 and can be as low as 1:1, which catalyst is more abrasion resistant and more favorably priced than previous catalysts and which makes possible high space-time-yields at simultaneously higher operating reliability.

According to this invention the problem is solved by intimately mixing the wet, dried or calcined precipitate obtained by coprecipitation of dissolved mobydenum and iron compound with up to 90 weight %, e.g., as low as 1 weight %, preferably 3 to 60 weight %, of titanium dioxide based on the water free coprecipitate, pasting the mixture with liquid and/or mold assist agents, in a given case after renewed calcination, and working to molded objects and subsequently heating these objects stepwise in an oxidizing atmosphere, for example within 24 hours, to a temperature between 350° and 600° C., preferably 400° to 500° C. and calcining at the final temperature for up to 24 hours. The heating between 350° and 600°C. can be for a time of 1 to 72 hours and the final calcining can be for a time as short as 0.5 hours.

In one variant of the process of production the precipitate can be calcined at 350° to 600° C., preferably at 400° to 500° C. for up to 24 hours. The calcining can be for as little as 0.5 hours. This calcining is before adding the titanium dioxide.

However, the mixture of dried or calcined precipitate and titanium dioxide prior to the working into molded objects can be calcined for up to 24 hours at 350° to 600° C., preferably at 400° to 500°C. The calcining can be for as little as 0.5 hour.

As previously pointed out especially good catalysts are obtained if the $MoO_3:Fe_2O_3$ ratio in the catalysts are below 10:1 and the $TiO_2$ content is 3 to 60 weight %. The lower limit on the $MoO_3:Fe_2O_3$ ratio can be that stated previously.

Other advantageous properties are obtained with catalysts according to the invention if there is provided a content of titanium dioxide up to 90 weight %, based on the sum of the oxidic compounds of molybdenum and iron. To be sure such catalysts do not have the maximum activity; their advantage is much more in the reduction in cost of the catalyst at practically unchanged, or often at even increased selectivity. The modification with higher amounts of titanium dioxide is of special interest if in a first step the main portion of the reactants are allowed to react with as high as possible selectivity using such catalysts and thereafter in a second step the still unreacted reaction gas is allowed to react on a catalyst with higher activity.

Unless otherwise indicated all parts and percentages are by weight.

Within the space of the process of production of the invention it has also been found suitable to first stepwise within 24 hours, heat the molded objects with the introduction of air to a temperature of 430°C. and finally to calcine for 5 hours at this temperature.

The preparation of the molded body can take place in the following manner. The mixture of the coprecipitate and titanium dioxide can be pressed into tablets of about 3-4 mm. diameter and height in a tablet press with addition of a mold lubricant, e.g., stearic acid. Another pressing procedure provides for pressing the mixture of the coprecipitate with titanium dioxide after forming a paste with a liquid mold lubricant, e.g., water, to form extrusions measuring 3 to 5 mm. by 3 to 5 mm.

If catalysts having an irregular particle shape are preferred then a mixture of the coprecipitate with titanium dioxide after addition of a liquid mold assist agent, e.g., water, can be spread out on a support and after drying in air broken into particles of about 3-4 mm. diameter. The invention goes beyond the catalysts obtained by the described process. This is characterized by a composition of oxidic compounds of molybdenum and iron with a $MoO_3:Fe_2O_3$ weight ratio below 10:1 and a content of up to 90 weight % titanium dioxide, the lower limits being as indicated above.

Finally the invention is concerned with the use of the novel catalysts in processes for the oxidation of methanol with oxygen containing gases, especially air, to form formaldehyde. The reaction can be carried out at conventional temperatures and pressures for such reaction, e.g., in a fixed bed reactor at a temperature of 240°–450°C. and a mol percent of methanol in the methanol-air mixture of 6.0 to 7.5%.

A high mechanical strength in th molded catalyst is necessary in order that there does not occur an undesired progressive drop in the pressure in the reaction tubes during operation due to the breaking of the molded catalyst. With increasing drop in pressure there would occur a reduction in output as well as an increase in side reactions, so far as there is not provided a compensatory increase in the pressure of the methanol-air mixture flowing in the reaction tubes. Because of the size of the required gas mixture this method of operation, however, is tied to a not immaterial increase in cost of operation. The mechanical strength of the catalyst therefore is of great significance as is also pointed out in German patent No. 1,144,252 and German patent No. 1,282,611.

The titanium dioxide content of the catalyst provided by the invention strongly increases the mechanical strength. While for example in German patent No. 1,144,252 there is stated an average breaking limit of 7.4 kg per particle (extruded cylinders 3.5 × 3.5 mm) for the molydenum oxide - iron oxide catalyst described therein having a weight ratio of Mo:Fe of 3.9 to 4.3, the breaking limit of the molybdenum-iron-titanium oxide catalysts of the present invention prepared by the process of example 1 of the present case is up to 120% higher as can be seen from the following Table 1.

TABLE 1

Catalyst (Extruded Object)

| Composition | | | Measurements mm | Average Breaking Limit kg/particle |
|---|---|---|---|---|
| %MoO$_3$ | %Fe$_2$O$_3$ | %TiO$_2$ | | |
| 74.2 | 15.8 | 10.0 | 3.5 × 3.5 | 16.7 |
| 57.5 | 11.9 | 30.6 | 3.5 × 3.5 | 13.9 |
| 44.3 | 8.5 | 47.2 | 3.5 × 3.5 | 8.5 |
| 67.5 | 14.3 | 18.2 | 2.8 × 2.9 | 10.2 |

Since the cost of the catalysts and tube bundle reactors are high it is worth striving for a high space-time-yield (kg formaldehyde per liter or kg of catalyst × hours). The space-time-yield is dependent upon the activity and selectivity of the catalyst and is limited by the effect of temperature. The titanium dioxide containing catalysts of the invention surprisingly have an especially high space-time-yield. It can, depending on the composition of the catalyst, amount to up to 2 kg HCHO/liter or kg of catalyst × hour (the apparent density of the TiO$_2$ containing catalysts in extruded articles of 3.5 × 3.5 mm. is about 1 kg/liter/. For molybdenum-iron oxide catalysts which do not contain titanium oxide according to German patent No. 1,144,252, German patent No. 1,282,611 and German offenlegungsschrift No. 1,667,270 there are obtained space-time-yields between 0.5 and 0.9 kg HCHO/liter catalyst × hour.

Besides a high space-time-yield low production costs are also desirable for a catalyst. With the usual mobydenum-iron oxide catalysts there are high raw material costs, especially due to the high molybdenum content. With the mixed molybdenum-iron titanium oxide catalysts of the invention the production costs are substantially lower because of the lower molybdenum contents. Thus the catalyst raw material costs are reduced about 25% by the addition of about 30 weight % TiO$_2$.

Besides the noted advantages possessed by the mixed catalysts of the invention there was found surprisingly the special advantage of a remarkably small dependence of the formaldehyde and carbon monoxide formation on temperature in the interesting reaction region.

The strongly exothermic reaction of methanol with oxygen to form formaldehyde and water proceeds with the setting free of 1190 kilogram calories per kg of methanol. In an undesired side reaction a part of the methanol on the catalyst, however, reacts to form carbon monoxide and water, whereby per kg of reacted methanol there arise 2850 kcal. At very high temperatures the methanol burns to carbon dioxide and water whereupon an additional 2100 kcal per kg of methanol are set free. If the side reaction to carbon monoxide takes place to too great an extent there occurs not only an undesired reduction in yield but also an increase in temperature in the catalyst which leads to an increase of the speed of reaction with further hastening of the side reaction and finally to complete burning of the methanol.

A good catalyst therefore should not only produce little carbon monoxide in the stationary working state but should also not react too much dependent upon temperature changes, above all on increases in temperature.

The temperature sensitivity of the catalyst for carrying out and regulating the reaction is of greater significance especially in tube reactors. If it is large, small fluctuations in the methanol concentration of the added gases, in the amount of added gas, in the distribution of the added gas to the individual reaction tubes, in the amount of cooling agent or in the temperature of the cooling agent quickly lead to a local overheating, on occasion even to the "run away" of the reactor. This danger is the greater the greater is the diameter of the catalyst tubes. An industrially regulatory treatment of the problem is made more difficult because a temperature probe cannot be placed in each catalyst tube, whose number in an industrial reactor amounts to several thousand.

Figure 2:
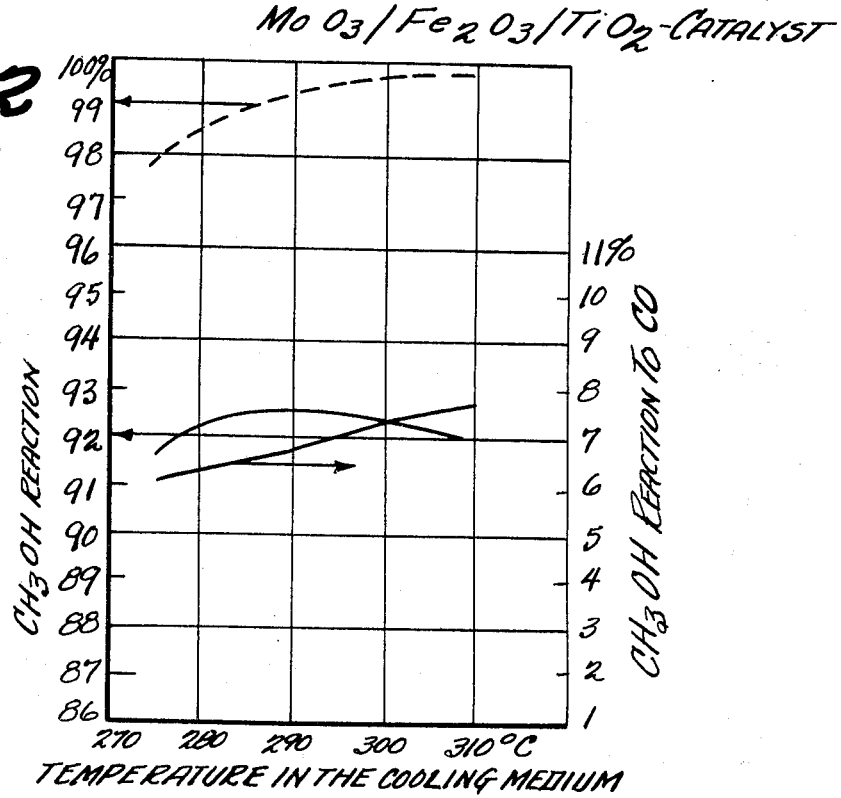

The damping influence of the titanium oxide content of the molybdenum-iron oxide catalyst of the invention on the temperature dependency of the formation of formaldehyde and carbon monoxide formation is seen from the curves set forth accompanying FIGS. 1 and 2 for the given amounts.

In FIGS. 1 and 2 there are set forth graphically the experimental results utilizing a tube reactor having an inner diameter of 15 mm and a filled catalyst length of 50 cm. and provided with a cooling jacket. The operating conditions correspond to those in the subsequent examples. With exception of the temperature of the cooling medium the experiments were run under identical conditions. FIG. 1 shows the results which were obtained with a molybdenum-iron oxide catalyst without TiO$_2$ addition (Composition of example 4); FIG. 2 shows the results which were produced by a molybdenum-iron oxide catalyst with a TiO$_2$ content of 30 weight % (composition of example 8). In FIG. 1 the highest formaldehyde yield (based on the methanol added) is at a cooling agent temperature of 265°C. (see the lower curve with the arrow to the left), in FIG. 2, the highest formaldehyde yield is at 288°C, (see the lower curve with the arrow to the left). The upper broken line curve with the arrow to the left in FIGS. 1 and 2 shows the total methanol reaction. The curve with the arrow to the right in FIGS. 1 and 2 shows the methanol reaction to carbon monoxide. On the abscissa of FIGS. 1 and 2 this is entered the cooling agent temperature.

It can be seeen from FIG. 1 that with pure molybdenum-iron oxide catalyst a markedly maximum formaldehyde formation is present and the latter falls off sharply with increasing temperature. After the maximum is exceeded there occurs very quickly and strongly the undesired formation of carbon monoxide which can be read off especially plainly from the exponential increase in the CO curve. In contrast as can be seen from FIG. 2 the molybdenum-iron-titanium oxide catalyst shows a very broad maximum for formaldehyde formation and above all does not show a steep falling off at higher temperature. This is expressed in reverse in the curve of carbon monoxide formation which is at a lower level than with the molybdenum-iron oxides catalyst and shows a substantially lower increase with increasing temperature.

A temperature increase of 20°C over the maximum formaldehyde formation caused by outside conditions (see above) brings about with the molybdenum-iron oxide catalyst a reduction in yield of formaldehyde of 2.1% (absolute) and an increase in carbon monoxide formation of 2.4%. With titanium dioxide containing catalyst the corresponding numbers are 0.4% and 1.0%.

The production of the mixed catalysts used in the invention can take place in various ways, for example by mixing an iron salt solution, for example an aqueous ferric chloride solution, with an aqueous ammonium heptamolybdate solution repeatedly washing the Mo-Fe-oxide precipitate mixing the washed precipitate with the $TiO_2$, filtering off the oxide mixture and drying the filter cake. The dried filter cake is homogenized with water and the paste obtained is pressed through a nozzle. The strands obtained is dried, broken and the molded bodies calcined.

In place of ferric chloride there can be used other water soluble iron salts such as ferric bromide, ferrous chloride, ferric nitrate, ferric sulfate or ferrous sulfate. In place of ammonium heptamolybdate there can be used sodium or potassium heptamolybdate.

EXAMPLE I

There were added to a warm solution of 0.617 kg of ammonium heptamolybdate in 12.4 liters of water at 60°C. with strong stirring within 30 minutes a solution of 0.34 kg of $FeCl_3.6H_2O$ in 6.8 liters of water, whereas a precipitate of molybdenum-iron oxides formed. The precipitate was allowed to settle until about 10 liters of clear solution could be decanted off. The Mo/Fe oxide precipitated was then treated with 10 liters of water and suspended by stirring. After again allowing the mixture to settle it was again decanted. In all the resuspension and decanting off was carried out six times.

After the last decantation there were mixed with the Mo/Fe-oxide precipitate 0.215 kg of $TiO_2$. The Mo/Fe/Ti-oxide mixture was separated off and finally dried for 2 days at 100°C. whereupon there were obtained 0.74 kg of Mo/Fe/Ti-oxide crude catalyst.

The further working up of the Mo/Fe/Te-oxide crude catalyst was accomplished by homogenizing with water in a mortar mill whereupon there was produced a paste having a water content of about 45 weight %. This product was divided in half with part (a) being pressed through a nozzle having a diameter of 4.7 mm and part (b) being pressed through a nozzle having a diameter of 4 mm.

The strands obtained were dried in air for 2 days and then broken into shaped bodies having an average length of (a) about 4.0 mm. and (b) about 3.3 mm. The shaped bodies were brought to a temperature of 430°C. within 24 hours while introducing air and held for 5 hours at this temperature. The finished mixed catalyst had a composition of 58.2 weight % $MoO_3$, 12.0 weight % $Fe_2O_3$ and 29.8 weight % $TiO_2$, a specific surface area(BET) of 9.5 m²/g and shaped body measurements of cross section (a) 3.5 mm diameter and 3.5 mm length and (b) 2.95 mm diameter and 3.0 mm length.

The average breaking limit of the shaped bodies was for (a) 15 kg and for (b) 9.9 kg.

For the production of mixed catalysts with a different Mo/Fe/Ti-oxide ratio the process described in example 1 was employed with only the amount of ammonium heptamolybdate or ferric chloride or $TiO_2$ being varied.

EXAMPLE II

There were poured into a fine steel tube having an inner diameter of 15 mm. 82 grams of the catalyst produced according to example 1(a), corresponding to a bed layer height of 49.9 cm.

There were led hourly through this reaction tube around which flowed oil at a temperature of 290°C. a mixture of 4 moles of $CH_3OH$ plus 57.5 moles of air at an entrance temperature of 250°C.

The $CH_3OH$ conversion was 98.8% whereby 3.69 moles of HCHO/hour (92.3% of theory) were obtained with a yield of 1.35 kg/kg catalyst × hour.

EXAMPLE III

There were poured into a fine steel tube having an inner diameter of 19 mm. 133.3 grams of the catalyst produced according to example 1(b) [bed layer height 47.8 cm.]

There were led hourly through this reaction tube a mixture of 3.70 moles of $CH_3OH$ plus 50.7 moles of air at an entrance temperature of 255°C. The oil bath around the reaction tube had a temperature of 290°C.

The $CH_3OH$ transformation was 99.35% thereby there were obtained 3.44 moles of HCHO/h . (93.0% of theory), HCHO— yield of 0.775 kg/kg catalyst × hour.

EXAMPLE IV 72 grams of a comparison catalyst produced according to example 1 but without the addition of $TiO_2$ and in the form of shaped bodies of about 3.5 × 3.5 mm. were filled into the reaction tube having an inner diameter of 15 mm. (bed layer height 47.2 cm.). The catalyst had a composition of 80.7 weight % $MoO_3$ plus 19.3 weight % $Fe_2O_3$. There were led over the catalyst hourly at an oil bath temperature of 270°C a mixture of 2 moles of $CH_3OH$ plus 28.65 moles of air at an entrance temperature of 240°C. Thereby 99.6% of the $CH_3OH$ was transformed and there were obtained 1.82 moles of HCHO/h . (91.4% of theory). HCHO— yield 0.76 kg/kg catalyst × hour.

EXAMPLE V

There were poured into the reaction tube having an inner diameter of 15 mm. 49 grams (bed layer height 35.2 cm.) of a catalyst produced according to example 1 having the composition 40.8 weight % $MoO_3$ plus 9.0 weight % $Fe_2O_3$ plus 50.2 weight % $TiO_2$. The catalyst shaped bodies measured 4.2 × 4.2 mm. (i.e., they were cylinders having a diameter of 4.2 cm. and a height of 4.2 mm.)

At an oil bath temperature of 320°C. there were introduced hourly into the reaction tube a mixture heated to 270°C. of 2.51 moles of $CH_3OH$ plus 35.7 moles of air, whereupon the $CH_3OH$ transformation was 97.1%. There were obtained 2.28 moles of HCHO/h (90.0% of theory). HCHO— yield 1.4 kg/kg catalyst × hour.

EXAMPLE VI 121.7 grams of the catalyst of example 5 were poured into the 19 mm. reaction tube (height of the bed layer 49.6 cm.) which was surrounded by 300°C hot oil. There were led through hourly a mixture of 3.84 moles of $CH_3OH$ plus 55.7 moles of air which had an entrance temperature of 245°C.

At a $CH_3OH$ conversion of 98.7% there were obtained 3.52 moles of HCHO/h (91.8% of theory). HCHO— yield 0.87 kg/kg catalyst × hour.

EXAMPLE VII

There were poured into the reaction tube having an inner diameter of 15 mm. 88 grams (bed layer height 46.5 cm. of catalyst produced according to example 1 and having the composition 67.6 weight % $MoO_3$ plus 13.6 weight % $Fe_2O_3$ plus 18.8 weight % $TiO_2$. The catalyst shaped bodies measured 3.1 × 3.1 mm.

At an oil bath temperature of 290°C., were led hourly over the catalyst bed a mixture of 2.25 moles of $CH_3OH$ plus 31.9 moles of air heated to an entrance temperature of 245°C. The $CH_3OH$ conversion was 99.1%, the HCHO yield 2.08 moles/h (92.4% of theory). HCHO— yield 0.71 kg/kg catalyst × hour.

EXAMPLE VIII

A Mo/Fe-oxide precipitate obtained by precipitating and washing as in example 1 was separated off, dried at 100°C for 24 hours and then calcined for 5 hours at 430°C. The 0.52 kg of Mo/Fe-oxide obtained together with 0.224 kg of $TiO_2$ were worked up with water to a homogeneous paste in a mortar mill, which paste was stretched out to 4 mm. thick on a support. After air drying for about 24 hours the pieces obtained were reduced to a particle size of 2.8–4.0 mm. and calcined as described in example 1. Composition of the catalyst: 56.5 weight % $MoO_3$ plus 13.4 weight % $Fe_2O_3$ plus 30.1 weight % $TiO_2$.

75 grams (height of the bed layer 44.8 cm.) of this catalyst were poured into the reaction tube having a 15 mm. inner diameter. The catalyst consisted of particles of the 2.8–4 mm. fraction.

At an oil bath temperature of 300°C, there were led over the catalyst layer hourly a mixture of 5.5 moles of $CH_3OH$ plus 71.0 moles of air heated to 260°C. The $CH_3OH$ conversion was 98.1%. There were obtained 5.06 mols/h of HCHO (92.1% of theory). HCHO— yield 2.02 kg/kg catalyst × hour.

EXAMPLE IX

There were placed in the reaction tube having an inner diameter of 15 mm. 80 grams (bed layer height 49 cm.) of the catalyst of example 8. This catalyst was thermally pretreated for the following experiment for 2 hours at 500°C.

At an oil bath temperature of 310°C, there were led through the reaction tube a mixture of 2.21 moles of $CH_3OH$. Conversion was 9.1% and the HCHO yield was 2.07 moles/h (93.5% of theory). HCHO— yield 0.775 kg/kg catalyst × hour.

EXAMPLE X

The reaction tube having an inner diameter of 15 mm. was filled with 79 grams (bed layer height 50.1 cm.) of a catalyst produced according to example 1 and having the composition 78.2 weight % $MoO_3$ plus 18.8 weight % $Fe_2O_3$ plus 3.0 weight % $TiO_2$. The shaped bodies of the catalyst measured 3.1 × 3.1 mm.

There were hourly passed through the reaction tube which was surrounded by circulating oil at 275°C. a mixture of 2.15 moles of $CH_3OH$ plus 32.1 moles of air heated to 245°C. The $CH_3OH$ was converted to an extent of 99.2%. There were obtained 1.98 moles/h (92.1% of theory) of formaldehyde which corresponded to a HCHO— yield of 0.75 kg/kg catalyst × hour.

EXAMPLE XI

A crude Mo/Fe/Ti-oxide catalyst obtained according to example 1 was dried for 2 days at 100°C. and calcined for 5 hours at 430°C. The calcined crude catalyst was treated with 3 weight % of stearic acid as a mold lubricant by means of a roller block and then pressed to tablets of about 4 × 4 mm. (i.e., diameter 4 mm., height 4 mm.) The tablets were brought to a temperature of 430°C., within 24 hours while introducing air and then calcined at this temperature for 5 hours. The composition of the catalyst was 57.2% $MoO_3$ plus 12.1% $Fe_2O_3$ plus 30.7% $TiO_2$. There were poured into the reaction tube having an inner diameter of 15 mm. 76 grams (height of the bed layer 48 cm.) of this catalyst.

At an oil bath temperature of 290°C., there were led hourly through the catalyst bed a mixture of 2.01 moles $CH_3OH$ plus 28.7 moles of air heated to 250°C. The $CH_3OH$ conversion was 99.3% and the HCHO yield was 1.85 moles/h (92.0% of theory). HCHO— yield 0.73 kg/kg catalyst × hour.

What is claimed is:

1. In a process of preparing formaldehyde by heat reacting methanol and an oxygen containing gas with a $MoO_3:Fe_2O_3$ containing catalyst the improvement comprising carrying out the reaction with the catalyst having an $MoO_3:Fe_2O_3$ weight ratio of between 1:1 and 10:1 prepared by coprecipitating molybdenum and iron as molybdenum oxide and iron oxide from an aqeuous mixture of a molybdenum salt containing molybdenum in an anionic form and an iron salt which is a water soluble ferrous or ferric salt, mixing titanium dioxide in an amount of 1 to 90 weight % of the total oxides with the coprecipitate and treating the mixture at 350° to 600°C. in an oxidizing atmosphere.

2. A process according to claim 1 wherein the molybdenum salt is ammonium heptamolybdate, sodium heptamolybdate, or potassium heptamolybdate, said catalyst consisting of $MoO_3$, $Fe_2O_3$ and $TiO_2$.

3. A process according to claim 2 wherein the catalyst is one which has been prepared by treatment of the mixture in the oxidizing atmosphere stepwise for a time of up to 24 hours to a temperature ranging from 350° to 600°C. followed by calcining at the final temperature in said range for up to 72 hours.

4. A process according to claim 2 wherein the salt is ammonium heptamolybdate.

5. A process according to claim 2 wherein the iron salt is ferrous chloride, ferric chloride, ferric bromide, ferric nitrate, ferric sulfate or ferrous sulfate.

6. A process according to claim 5 wherein the catalyst consists essentially of $MoO_3$, $Fe_2O_3$ and $TiO_2$.

7. A process according to claim 2 wherein the catalyst consists essentially of $MoO_3$ $Fe_2O_3$ and $TiO_2$.

8. A process according to claim 1 wherein the titanium dioxide is 3 to 60 weight % of the total oxides.

9. A process according to claim 2 wherein the weight ratio of $MoO_3:Fe_2O_3:TiO_2$ is 9–6:1–4:90.

10. A process according to claim 3 wherein the titanium dioxide is 3 to 60 weight % of the total of $MoO_3$ plus $Fe_2O_3$ plus $TiO_2$.

* * * * *